(12) United States Patent
Desjardin et al.

(10) Patent No.: US 11,141,191 B2
(45) Date of Patent: Oct. 12, 2021

(54) SURGICAL ACCESS ASSEMBLY

(71) Applicant: Covidien LP, Mansfield, MA (US)

(72) Inventors: Kevin Desjardin, North Haven, CT (US); Astley C. Lobo, North Haven, CT (US)

(73) Assignee: Covidien LP, Mansfield, MA (US)

( * ) Notice: Subject to any disclaimer, the term of this patent is extended or adjusted under 35 U.S.C. 154(b) by 77 days.

(21) Appl. No.: 16/743,003

(22) Filed: Jan. 15, 2020

(65) Prior Publication Data

US 2021/0212724 A1    Jul. 15, 2021

(51) Int. Cl.
*A61B 1/32* (2006.01)
*A61B 17/34* (2006.01)
*A61B 17/00* (2006.01)

(52) U.S. Cl.
CPC .............. *A61B 17/3423* (2013.01); *A61B 2017/00477* (2013.01); *A61B 2017/00557* (2013.01); *A61B 2017/3419* (2013.01)

(58) Field of Classification Search
CPC combination set(s) only.
See application file for complete search history.

(56) References Cited

U.S. PATENT DOCUMENTS

| | | |
|---|---|---|
| 1,780,912 A | 11/1930 | Gau |
| 1,810,466 A | 6/1931 | Deutsch |
| 2,313,164 A | 3/1943 | Nelson |
| 2,541,516 A | 2/1951 | Ivory et al. |
| 2,812,758 A | 11/1957 | Blumenschein |
| 3,782,370 A | 1/1974 | McDonald |
| 3,807,393 A | 4/1974 | McDonald |
| 3,965,890 A | 6/1976 | Gauthier |
| 4,130,113 A | 12/1978 | Graham |
| 4,263,899 A | 4/1981 | Burgin |
| 4,553,537 A | 11/1985 | Rosenberg |
| 5,007,900 A | 4/1991 | Picha et al. |
| 5,052,374 A | 10/1991 | Alvarez-Jacinto |
| 5,080,088 A | 1/1992 | LeVahn |
| 5,125,396 A | 6/1992 | Ray |
| 5,169,387 A | 12/1992 | Kronner |
| 5,231,974 A | 8/1993 | Giglio et al. |
| 5,232,451 A | 8/1993 | Freitas et al. |

(Continued)

FOREIGN PATENT DOCUMENTS

| | | |
|---|---|---|
| DE | 10001695 A1 | 2/2001 |
| DE | 102009014527 A1 | 9/2010 |

(Continued)

OTHER PUBLICATIONS

European Search Report dated Jun. 10, 2021, issued in corresponding EP Appln. No. 21151684, 9 pages.

*Primary Examiner* — Sameh R Boles

(57) ABSTRACT

A surgical access assembly includes a surgical syringe and a balloon trocar. The balloon trocar has a collar in fluid communication with a balloon. The collar has a check valve configured to control the passage of inflation medium to and from the balloon. The syringe has a barrel and a plunger. The barrel of the syringe has a tip configured for engaging the check valve to discharge the inflation medium into the balloon. The syringe has a lateral extension configured for receipt in the check valve for opening the check valve to rapidly discharge inflation medium from the balloon.

8 Claims, 4 Drawing Sheets

(56) References Cited

U.S. PATENT DOCUMENTS

| | | |
|---|---|---|
| 5,269,754 A | 12/1993 | Rydell |
| 5,279,575 A | 1/1994 | Sugarbaker |
| 5,330,501 A | 7/1994 | Tovey et al. |
| 5,346,484 A | 9/1994 | Van Lindert |
| 5,391,156 A | 2/1995 | Hildwein et al. |
| 5,437,683 A | 8/1995 | Neumann et al. |
| 5,445,615 A | 8/1995 | Yoon |
| 5,460,170 A | 10/1995 | Hammerslag |
| 5,480,410 A | 1/1996 | Cuschieri et al. |
| 5,490,843 A | 2/1996 | Hildwein et al. |
| 5,503,617 A | 4/1996 | Jako |
| 5,520,610 A | 5/1996 | Giglio et al. |
| 5,524,644 A | 6/1996 | Crook |
| 5,556,385 A | 9/1996 | Andersen |
| 5,562,677 A | 10/1996 | Hildwein et al. |
| 5,653,705 A | 8/1997 | de la Torre et al. |
| 5,697,891 A | 12/1997 | Hori |
| 5,728,103 A | 3/1998 | Picha et al. |
| 5,755,660 A | 5/1998 | Tyagi |
| 5,755,661 A | 5/1998 | Schwartzman |
| 5,772,583 A | 6/1998 | Wright et al. |
| 5,776,110 A | 7/1998 | Guy et al. |
| 5,779,629 A | 7/1998 | Hohlen |
| 5,788,630 A | 8/1998 | Furnish |
| 5,803,921 A | 9/1998 | Bonadio |
| 5,810,721 A | 9/1998 | Mueller et al. |
| 5,846,193 A | 12/1998 | Wright |
| 5,875,782 A | 3/1999 | Ferrari et al. |
| 5,879,291 A | 3/1999 | Kolata et al. |
| 5,906,577 A | 5/1999 | Beane et al. |
| 5,908,382 A | 6/1999 | Koros et al. |
| 5,931,778 A | 8/1999 | Furnish |
| 5,935,107 A | 8/1999 | Taylor et al. |
| 5,944,736 A | 8/1999 | Taylor et al. |
| 5,951,466 A | 9/1999 | Segermark et al. |
| 5,951,467 A | 9/1999 | Picha et al. |
| 5,957,835 A | 9/1999 | Anderson et al. |
| 5,967,972 A | 10/1999 | Santilli et al. |
| 5,993,385 A | 11/1999 | Johnston et al. |
| 6,024,736 A | 2/2000 | de la Torre et al. |
| 6,033,362 A | 3/2000 | Cohn |
| 6,033,425 A | 3/2000 | Looney et al. |
| 6,036,641 A | 3/2000 | Taylor et al. |
| 6,048,309 A | 4/2000 | Flom et al. |
| 6,074,380 A | 6/2000 | Byrne et al. |
| 6,113,535 A | 9/2000 | Fox et al. |
| 6,120,436 A | 9/2000 | Anderson et al. |
| 6,132,370 A | 10/2000 | Furnish et al. |
| 6,142,935 A | 11/2000 | Flom et al. |
| 6,159,231 A | 12/2000 | Looney et al. |
| 6,162,172 A | 12/2000 | Cosgrove et al. |
| 6,231,506 B1 | 5/2001 | Hu et al. |
| 6,254,533 B1 | 7/2001 | Fadem et al. |
| 6,254,534 B1 | 7/2001 | Butler et al. |
| 6,283,912 B1 | 9/2001 | Hu et al. |
| 6,309,349 B1 | 10/2001 | Bertolero et al. |
| 6,312,377 B1 | 11/2001 | Segermark et al. |
| 6,331,158 B1 | 12/2001 | Hu et al. |
| 6,332,468 B1 | 12/2001 | Benetti |
| 6,354,995 B1 | 3/2002 | Hoftman et al. |
| 6,361,492 B1 | 3/2002 | Santilli |
| 6,382,211 B1 | 5/2002 | Crook |
| 6,443,957 B1 | 9/2002 | Addis |
| 6,450,983 B1 | 9/2002 | Rambo |
| 6,458,079 B1 | 10/2002 | Cohn et al. |
| 6,500,116 B1 | 12/2002 | Knapp |
| 6,517,563 B1 | 2/2003 | Paolitto et al. |
| 6,547,725 B1 | 4/2003 | Paolitto et al. |
| 6,585,442 B2 | 7/2003 | Brei et al. |
| 6,599,240 B2 | 7/2003 | Puchovsky et al. |
| 6,599,292 B1 | 7/2003 | Ray |
| 6,616,605 B2 | 9/2003 | Wright et al. |
| 6,652,454 B2 | 11/2003 | Hu et al. |
| 6,723,044 B2 | 4/2004 | Pulford et al. |
| 6,730,021 B2 | 5/2004 | Vassiliades, Jr. et al. |
| 6,730,022 B2 | 5/2004 | Martin et al. |
| 6,746,396 B1 | 6/2004 | Segermark et al. |
| 6,746,467 B1 | 6/2004 | Taylor et al. |
| 6,814,078 B2 | 11/2004 | Crook |
| 6,814,700 B1 | 11/2004 | Mueller et al. |
| 6,840,951 B2 | 1/2005 | de la Torre et al. |
| 6,846,287 B2 | 1/2005 | Bonadio et al. |
| 6,958,037 B2 | 10/2005 | Ewers et al. |
| 7,033,319 B2 | 4/2006 | Pulford et al. |
| 7,052,454 B2 | 5/2006 | Taylor |
| 7,144,368 B2 | 12/2006 | Larson et al. |
| 7,147,599 B2 | 12/2006 | Phillips et al. |
| 7,179,225 B2 | 2/2007 | Shluzas et al. |
| 7,195,592 B2 | 3/2007 | Ravikumar et al. |
| 7,220,228 B2 | 5/2007 | Hu et al. |
| 7,226,451 B2 | 6/2007 | Shluzas et al. |
| 7,229,408 B2 | 6/2007 | Douglas et al. |
| 7,238,154 B2 | 7/2007 | Ewers et al. |
| 7,261,688 B2 | 8/2007 | Smith et al. |
| 7,270,632 B2 | 9/2007 | Santilli |
| 7,300,399 B2 | 11/2007 | Bonadio et al. |
| 7,344,495 B2 | 3/2008 | Ravikumar et al. |
| 7,387,126 B2 | 6/2008 | Cox et al. |
| 7,393,322 B2 | 7/2008 | Wenchell |
| 7,473,222 B2 | 1/2009 | Dewey et al. |
| 7,507,202 B2 | 3/2009 | Schoellhorn |
| 7,507,235 B2 | 3/2009 | Keogh et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,566,302 B2 | 7/2009 | Schwer |
| 7,585,277 B2 | 9/2009 | Taylor et al. |
| 7,594,888 B2 | 9/2009 | Raymond et al. |
| 7,597,688 B1 | 10/2009 | Masson |
| 7,650,887 B2 | 1/2010 | Nguyen et al. |
| 2001/0002429 A1 | 5/2001 | Hu et al. |
| 2001/0020121 A1 | 9/2001 | Hu et al. |
| 2001/0041827 A1 | 11/2001 | Spence et al. |
| 2002/0004628 A1 | 1/2002 | Hu et al. |
| 2002/0095139 A1 | 7/2002 | Keogh et al. |
| 2002/0099269 A1 | 7/2002 | Martin et al. |
| 2002/0099271 A1 | 7/2002 | Knapp |
| 2002/0137989 A1 | 9/2002 | Clem et al. |
| 2003/0191371 A1 | 10/2003 | Smith et al. |
| 2004/0049099 A1 | 3/2004 | Ewers et al. |
| 2004/0054353 A1 | 3/2004 | Taylor |
| 2004/0059192 A1 | 3/2004 | Cartier et al. |
| 2004/0225195 A1 | 11/2004 | Spence et al. |
| 2005/0096508 A1 | 5/2005 | Valentini et al. |
| 2005/0171403 A1 | 8/2005 | Paolitto et al. |
| 2005/0228232 A1 | 10/2005 | Gillinov et al. |
| 2005/0267336 A1 | 12/2005 | Bertolero et al. |
| 2005/0283050 A1 | 12/2005 | Gundlapalli et al. |
| 2006/0004261 A1 | 1/2006 | Douglas |
| 2006/0089537 A1 | 4/2006 | Schoellhorn |
| 2006/0106416 A1 | 5/2006 | Raymond et al. |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0155170 A1 | 7/2006 | Hanson et al. |
| 2006/0190022 A1 | 8/2006 | Beyar et al. |
| 2007/0027364 A1 | 2/2007 | Schwer |
| 2007/0073110 A1 | 3/2007 | Larson et al. |
| 2007/0073248 A1 | 3/2007 | Moenning |
| 2008/0132766 A1 | 6/2008 | Dant et al. |
| 2008/0234550 A1 | 9/2008 | Hawkes et al. |
| 2009/0198216 A1 | 8/2009 | Muni et al. |
| 2009/0204067 A1 | 8/2009 | Abu-Halawa |
| 2009/0221960 A1* | 9/2009 | Albrecht ............ A61B 17/3421 604/103.03 |
| 2009/0265941 A1 | 10/2009 | Kurrus |
| 2009/0299148 A1 | 12/2009 | White et al. |
| 2010/0081990 A1 | 4/2010 | Swisher |
| 2010/0210916 A1 | 8/2010 | Hu et al. |
| 2010/0234689 A1 | 9/2010 | Wagner et al. |
| 2011/0288522 A1 | 11/2011 | Hollowell et al. |
| 2012/0289784 A1 | 11/2012 | Kucklick |
| 2014/0276869 A1 | 9/2014 | Tatsumi |

(56) References Cited

U.S. PATENT DOCUMENTS

| | | |
|---|---|---|
| 2017/0135721 A1 | 5/2017 | Pacak et al. |
| 2018/0271557 A1 | 9/2018 | Buyda et al. |
| 2019/0059937 A1 | 2/2019 | Buyda et al. |

FOREIGN PATENT DOCUMENTS

| | | |
|---|---|---|
| EP | 0177177 A2 | 4/1986 |
| EP | 2168626 A2 | 3/2010 |
| EP | 2179699 A1 | 4/2010 |
| EP | 2196161 A1 | 6/2010 |
| EP | 2228014 A1 | 9/2010 |
| EP | 2228024 A1 | 9/2010 |
| EP | 2238931 A1 | 10/2010 |
| EP | 2417922 A1 | 2/2012 |
| GB | 2275420 A | 8/1994 |
| WO | 9500197 A1 | 1/1995 |
| WO | 9515715 A1 | 6/1995 |
| WO | 0108563 A2 | 2/2001 |
| WO | 03034908 A2 | 5/2003 |
| WO | 2005089655 A1 | 9/2005 |
| WO | 2007106750 A2 | 9/2007 |
| WO | 2010136805 A1 | 12/2010 |
| WO | 2011079374 A1 | 7/2011 |
| WO | 2011090427 A1 | 7/2011 |

\* cited by examiner

SURGICAL ACCESS ASSEMBLY

FIELD

The present technology relates generally to surgical access devices and more particularly to a surgical access assembly for use in a minimally invasive surgical procedure.

BACKGROUND

Minimally invasive surgical procedures including both endoscopic and laparoscopic procedures permit surgery to be performed on organs, tissues, and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula accessing the abdominal cavity to perform one or more surgical tasks. An interior of the cannula may include a seal to establish a substantially fluid-tight seal about the instrument to preserve the integrity of the pneumoperitoneum.

While minimally invasive surgical procedures have proven to be quite effective in surgery, several limitations remain. For example, the cannula which is subjected to the pressurized environment, i.e., the pneumoperitoneum, may exhibit a tendency to back out of the incision in the abdominal wall particularly during manipulation of the instrument within the cannula. Conventional cannulas may incorporate an inflatable balloon at the end of the cannula in an effort to resist withdrawal of the cannula from the tissue site. A syringe may be coupled to the cannula and actuated to either inflate or deflate the balloon.

SUMMARY

The techniques of this disclosure generally relate to a surgical access assembly including a balloon trocar for providing access to a surgical cavity within a patient (e.g., an abdominal cavity) and a surgical syringe for injecting inflation medium and withdrawing inflation medium into and from a balloon of the balloon trocar. In accordance with one aspect, the surgical access assembly includes a surgical cannula assembly and a syringe. The surgical cannula assembly has an elongated cannula member, an expandable member mounted to a distal end portion of the cannula member, and a collar coupled to a proximal end portion of the cannula member. The cannula member defines a longitudinal passageway and the collar is in fluid communication with the expandable member. The collar has a check valve configured to control the passage of inflation medium to and from the expandable member. The syringe includes a barrel, a plunger, and a lateral extension. The barrel defines an internal chamber and has a distal end portion configured for engaging the check valve to discharge the inflation medium into the expandable member. The plunger has a distal end portion configured for receipt in the internal chamber. The lateral extension extends from the syringe and is configured for receipt in the check valve for opening the check valve.

In aspects, the plunger may have a proximal end portion, and the lateral extension may extend from the proximal end portion of the plunger.

In aspects, the proximal end portion of the plunger may have a thumb press, and the lateral extension may extend radially outward from the thumb press.

In aspects, the lateral extension may have a tab extending radially outward from an outer periphery of the thumb press.

In aspects, the barrel may have a proximal end portion, and the lateral extension may extend outward from the proximal end portion of the barrel.

In aspects, the lateral extension of the syringe may be configured to open the check valve to allow for the inflation medium to pass from the expandable member and out of the collar.

In aspects, the lateral extension may be configured to be received in the check valve, such that the syringe is fixed in a position perpendicular to the cannula member.

In aspects, the check valve may be a diaphragm check valve, a swing check valve, a ball check valve, an in-line check valve, a lift-check valve, or a stop-check valve.

In accordance with another aspect of the disclosure, a surgical syringe is provided and includes a barrel, a plunger, and a tab extending laterally outward from a proximal end portion of the syringe. The barrel defines an internal chamber and has a distal tip configured for discharging inflation medium. The plunger has a distal end portion configured for receipt in the internal chamber.

In aspects, a method of gaining access to a surgical cavity is provided and includes: positioning an expandable member of a balloon trocar through an opening and into a surgical cavity; actuating a plunger of a syringe, thereby injecting inflation medium from the syringe into the expandable member to expand the expandable member; inserting a lateral extension of the syringe into a check valve of the balloon trocar to open the check valve; and removing the expandable member from the surgical cavity, thereby transferring the inflation medium out of the expandable member and through the check valve.

In aspects, the method may further include inserting a distal tip of a barrel of the syringe into the check valve prior to actuating the plunger; and detaching the distal tip of the barrel from the check valve prior to inserting the lateral extension of the syringe into the check valve and after actuating the plunger.

In aspects, inserting the lateral extension into the check valve may include fixing the syringe in a position perpendicular to the balloon trocar.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Various aspects and features of the present disclosure are described hereinbelow with references to the drawings, wherein.

DETAILED DESCRIPTION

Particular aspects of the present disclosure are described hereinbelow with reference to the accompanying drawings. However, it is to be understood that the disclosed aspects are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure.

In general, the present disclosure provides a syringe for use with a balloon trocar. The syringe has a surface feature configured for selective receipt in a check valve of the trocar balloon. Upon inserting the surface feature of the syringe into the check valve, inflation medium within a balloon of the balloon trocar is released by the action of removing the balloon trocar from the surgical site. In this way, a clinician may more quickly withdraw the inflation medium from the balloon without having to connect a distal tip of the syringe to the balloon trocar and retract the plunger of the syringe.

Figure 1:
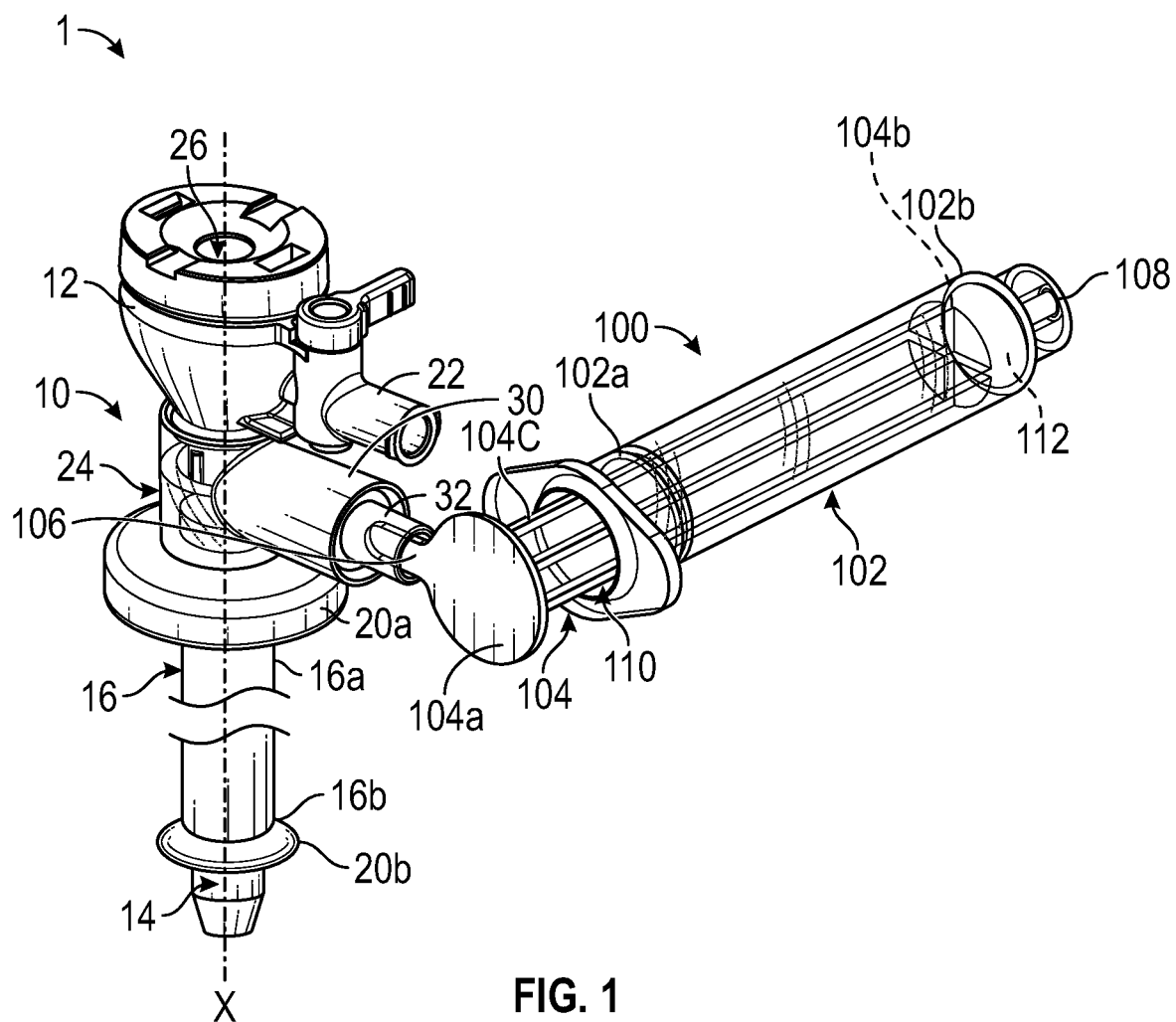
FIG. 1 is a perspective view illustrating a surgical access assembly including a syringe connected to a check valve of a balloon trocar.
Figure 2:
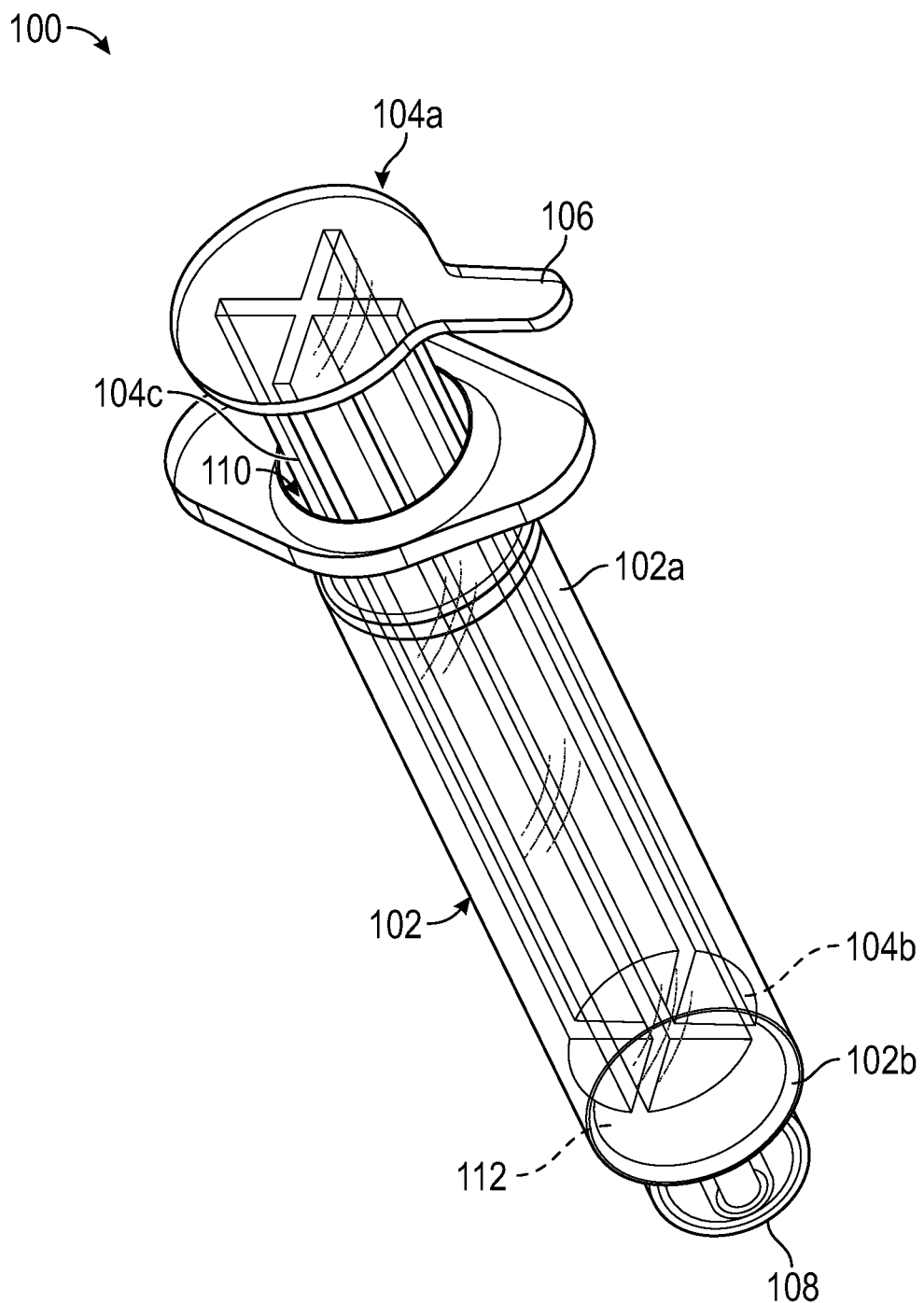
FIG. 2 is a perspective view illustrating the syringe of FIG. 1.

FIGS. 1 and 2 illustrate a surgical access assembly 1 generally including a surgical cannula assembly or balloon trocar 10, and a surgical syringe 100 for use with the balloon trocar 10. The balloon trocar 10 is intended to permit access to an insufflated abdominal cavity during a laparoscopic procedure to permit the introduction of a surgical instrument for performing various surgical tasks on internal organs within the cavity. The surgical instrument may be a surgical instrument such as laparoscopic or endoscopic clip appliers, graspers, dissectors, retractors, staplers, laser probes, photographic devices, tubes, endoscopes and laparoscopes, electro-surgical devices and the like. An obturator (not explicitly shown) may be positioned in the balloon trocar 10 to facilitate access to the abdominal cavity. The obturator may be any conventional obturator having a penetrating tip configured to penetrate tissue.

The balloon trocar 10 includes a cannula housing 12, an elongated cannula member 14 extending distally from the cannula housing 12, an outer sleeve 16 coaxially mounted over the cannula member 14, and proximal and distal expandable members or balloons 20a, 20b formed with the sleeve 16. The cannula housing 12 is dimensioned for engagement by the clinician and may include one or more internal seals (not shown) adapted to establish a seal about a surgical instrument introduced therethrough. The cannula housing 12 also may include an insufflation connector 22 (e.g., a luer connector) for connecting to a source of insufflation fluids (not shown) for delivery within, e.g., the abdominal cavity. The cannula member 14 defines a longitudinal axis "X" along which the cannula member 14 extends. The cannula member 14 defines a longitudinal passageway 26 to permit passage of the surgical instrument. The longitudinal passageway 26 is also in fluid communication with the insufflation connector 22 to convey insufflation fluids into the abdominal cavity to establish and/or maintain the pneumoperitoneum.

The proximal and distal expandable members 20a, 20b are coupled to respective proximal and distal portions of the outer sleeve 16 and are coaxially mounted about proximal and distal portions of the cannula member 14, respectively. In one aspect, the expandable members 20b, 20b are monolithically formed with the outer sleeve 16 from, e.g., a suitable elastomeric material. Each of the proximal and distal expandable members 20a, 20b defines a cavity or inner chamber therein, and the sleeve 16 defines a longitudinal channel (not explicitly shown) in communication with the cavity of each of the proximal and distal expandable members 20a, 20b. The proximal and distal expandable members 20a, 20b one of expand radially outwardly or retract radially inward upon passage of inflation media (e.g., air, water, gas, etc.) via a collar 24. In aspects, the balloon trocar 10 may only have the distal expandable member 20b.

The collar 24 of the balloon trocar 10 is positioned adjacent the cannula housing 12 and about the proximal portion of the cannula member 14. The collar 24 forms a fluid-tight seal with the proximal portion of the sleeve 16 to facilitate passage of inflation medium into the channel of the sleeve 16 and ultimately into the expandable members 20a, 20b. The collar 24 has a tube or port 30 extending laterally outward therefrom. The port 30 is configured as both an inlet and an outlet for the inflation media. The port 30 includes a check valve 32 disposed therein configured to transition between open and closed states in response to a mechanical actuation from an external feature, as will be described. In aspects, the check valve 32 may be any suitable type of valve, such as, for example, a diaphragm check valve, a swing check valve, a ball check valve, an in-line check valve, a lift-check valve, or a stop-check valve.

For a more detailed description of various aspects of the balloon trocar 10, reference may be made to U.S. Patent Application Publication No. 2019/0059937, filed on Jul. 24, 2018, the entire contents of which are incorporated by reference herein.

With continued reference to FIGS. 1 and 2, the syringe 100 of the surgical access assembly 1 includes a barrel 102, a plunger 104, and a lateral extension or tab 106 extending outwardly from the plunger 104. The barrel 102 defines an internal chamber or reservoir 110 and has a proximal end portion 102a and a distal end portion 102b. The distal end portion 102b of the barrel 102 has a distal tip 108 configured for receipt in the check valve 32 of the balloon trocar 10 to open the check valve 32 and discharge the inflation medium into the expandable members 20a, 20b upon an actuation of the plunger 104. In aspects, the pressure of the inflation medium may cause the check valve 32 to open rather than the insertion of the distal tip 108 into the port 30. The plunger 104 has a proximal end portion 104a, a distal end portion 104b, and a shaft 104c extending therebetween. The distal end portion 104b has a stopper 112 at its distal end for receipt in the internal chamber 110 of the barrel 102 and is configured to move fluid (e.g., inflation medium) into and out of the internal chamber 110.

The proximal end portion 104a of the plunger 104 may be a thumb press having a circular, planar shape. The lateral extension 106 of the syringe 100 extends laterally from an outer periphery of the thumb press 104a and is perpendicular relative to a longitudinal axis defined by the shaft 104c of the plunger 104. The lateral extension 106 may be monolithically formed with the thumb press 104a or otherwise coupled to the thumb press 104a. The lateral extension 106 may be planar, substantially oval, and configured for receipt in the check valve 32 for opening the check valve 32. In aspects, the lateral extension 106 may assume any shape suitable for being received in the port 30 to open the check valve 32 while allowing for inflation medium to move passed the lateral extension 106 and out of the balloon trocar 10. In aspects, the lateral extension 106 may extend from any suitable portion of the plunger 104.

In use, the surgical access assembly 1 may be used in a minimally invasive surgery to provide access to an underlying cavity, e.g., an abdominal cavity. In one methodology, the abdominal cavity is insufflated to establish a pneumoperitoneum. The obturator is positioned within the balloon trocar 10 and the assembled unit is advanced into an abdominal wall while the expandable members 20a, 20b are in a deflated state.

Upon positioning the distal expandable member 20b adjacent the abdominal wall, a clinician may insert the distal tip 108 of the syringe 100 into the port 30 of the collar 24 of the balloon trocar 10, thereby opening the check valve 32. With inflation medium pre-loaded in the internal chamber 110 of the barrel 102 of the syringe 100, the clinician may press down on the thumb press 104a of the plunger 104 to transfer the inflation medium (e.g., air) from the syringe 100, through the opened check valve 32, and into the expandable members 20a, 20b. After inflating the expandable members 20a, 20b to a suitable extent, the distal tip 108 of the syringe 100 may be removed from the port 30 of the balloon trocar 10, thereby allowing the check valve 32 to close and maintain the expandable members 20a, 20b in the expanded condition. In the expanded or at least partially expanded condition, the distal expandable member 20b will resist withdrawal of the balloon trocar 10 from the abdominal cavity while also providing a seal within the internal surface of the abdominal wall, minimizing passage of fluids, including inflation fluids, from the abdominal cavity.

To withdraw the balloon trocar 10 from the abdominal cavity, the tab 106 of the plunger 104 of the syringe 100 may be inserted into the port 30. Upon inserting the tab 106 of the syringe 100 into the port 30, the tab 106 mechanically opens the check valve 32 (e.g., the tab 106 engages and inwardly moves a valve disk or ball of the check valve 32). With the check valve 32 held in the open state by the tab 106, the clinician may begin to withdraw the balloon trocar 10 from the abdominal cavity, whereby the inflation medium is forced out of the expandable members 20a, 20b by the abdominal wall and out of the balloon trocar 10 via the opened check valve 32. In this way, the steps of deflating the expandable members 20a, 20b and removing the balloon trocar 10 from the surgical site occur concurrently.

Figure 3:
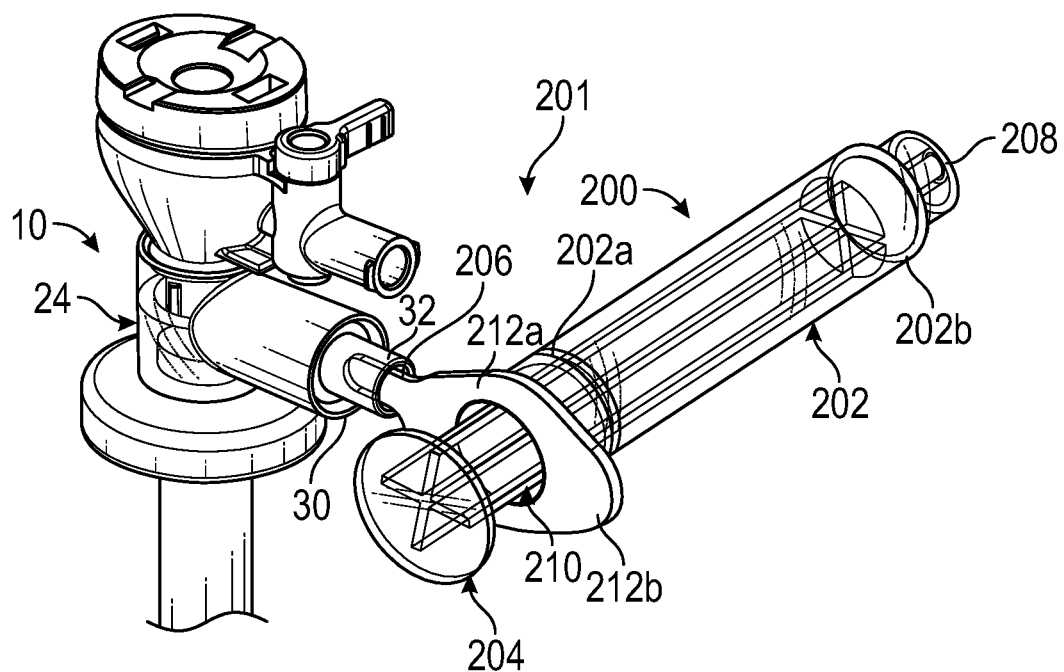
FIG. 3 is a perspective view illustrating a surgical access assembly including a syringe connected to the check valve of the balloon trocar of FIG. 1.
Figure 4:
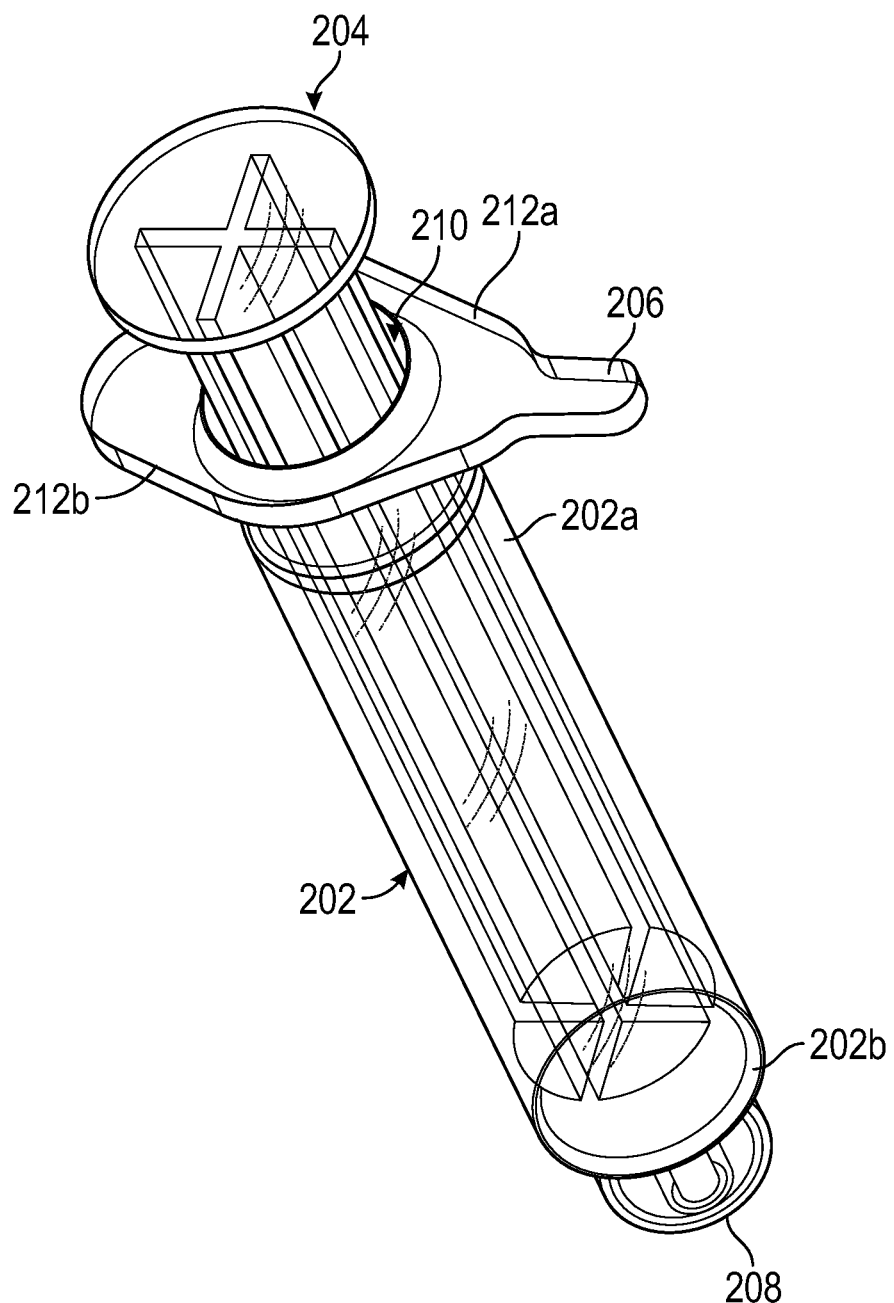
FIG. 4 is a perspective view illustrating the syringe of FIG. 3.

FIGS. 3 and 4 illustrate another surgical access assembly 201, similar to the surgical access assembly 1 of FIGS. 1 and 2. The surgical access assembly 201 includes the balloon trocar 10 of FIG. 1 and a surgical syringe 200 for use with the balloon trocar 10, similar to the surgical syringe 100 of FIGS. 1 and 2. The surgical syringe 200 generally includes a barrel 202 and a plunger 204. The barrel 202 defines an internal chamber or reservoir 210 and has a proximal end portion 202a and a distal end portion 202b. The distal end portion 202b of the barrel 202 has a distal tip 208 configured for receipt in the check valve 32 of the balloon trocar 10 to open the check valve 32 and discharge the inflation medium into the expandable members 20a, 20b (FIG. 1) upon an actuation of the plunger 204.

The surgical syringe 200 differs from the surgical syringe 100 of FIGS. 1 and 2 by having a lateral extension or tab 206 extending from the proximal end portion 202a of the barrel 202. More specifically, the barrel 202 has a flange, such as, for example, wings 212a, 212b extending radially outward from opposite sides of the barrel 202. The lateral extension 206 is monolithically formed with or otherwise coupled to one of the wings 212a, 212b. The lateral extension 206 has a reduced width relative to the wings 212a, 212b to allow for insertion of the lateral extension 206 into the port 30 to open the check valve 32. In aspects, the lateral extension 206 may extend from any suitable portion of the barrel 202.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A surgical access assembly, comprising: a surgical cannula assembly including:
an elongated cannula member having proximal and distal end portions and defining a longitudinal passageway; an expandable member mounted to the distal end portion of the cannula member; and a collar coupled to the proximal end portion of the cannula member and in fluid communication with the expandable member, the collar having a check valve configured to control the passage of inflation medium to and from the expandable member; and a syringe including: a barrel defining an internal chamber and having a distal end portion configured for engaging the check valve to discharge the inflation medium into the expandable member; a plunger having a distal end portion configured for receipt in the internal chamber; and a lateral extension extending from the syringe and configured for receipt in the check valve for opening the check valve, wherein the plunger has a proximal end portion, the lateral extension extending from the proximal end portion of the plunger.

2. The surgical access assembly according to claim 1, wherein the proximal end portion of the plunger has a thumb press, the lateral extension extending radially outward from the thumb press.

3. The surgical access assembly according to claim 2, wherein the lateral extension is a tab extending radially outward from an outer periphery of the thumb press.

4. The surgical access assembly according to claim 1, wherein the barrel has a proximal end portion, the lateral extension extending outward from the proximal end portion of the barrel.

5. The surgical access cannula assembly according to claim 1, wherein the lateral extension of the syringe is configured to open the check valve to allow for the inflation medium to pass from the expandable member and out of the collar.

6. The surgical access assembly according to claim 5, wherein the lateral extension is configured to be received in the check valve, such that the syringe is fixed in a position perpendicular to the cannula member.

7. The surgical access assembly according to claim 1, wherein the check valve is a diaphragm check valve, a swing check valve, a ball check valve, an in-line check valve, a lift-check valve, or a stop-check valve.

8. A surgical access assembly, comprising: a surgical cannula assembly including:
an elongated cannula member having proximal and distal end portions and defining a longitudinal passageway; an expandable member mounted to the distal end portion of the cannula member; and a collar coupled to the proximal end portion of the cannula member and in fluid communication with the expandable member, the collar having a check valve configured to control the passage of inflation medium to and from the expandable member; and a syringe including: a barrel defining an internal chamber and having a distal end portion configured for engaging the check valve to discharge the inflation medium into the expandable member; a plunger having a distal end portion configured for receipt in the internal chamber; and a lateral extension extending from the syringe and configured for receipt in the check valve for opening the check valve, wherein the lateral extension of the syringe is configured to open the check valve to allow for the inflation medium to pass from the expandable member and out of the collar.

* * * * *